May 7, 1940. J. F. STYER Plant Pat. 392

CHRYSANTHEMUM PLANT

Filed July 11, 1939

INVENTOR
John Franklin Styer
By Orville M Kile
Plant Patent Agt

Patented May 7, 1940

Plant Pat. 392

UNITED STATES PATENT OFFICE

392

CHRYSANTHEMUM PLANT

John Franklin Styer, Concordville, Pa.

Application July 11, 1939, Serial No. 283,886

1 Claim. (Cl. 47—60)

Figure 1:
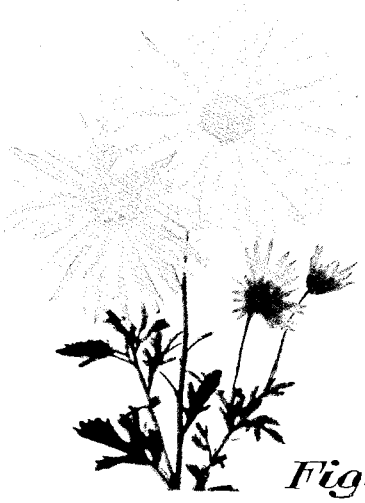
Figure 2:
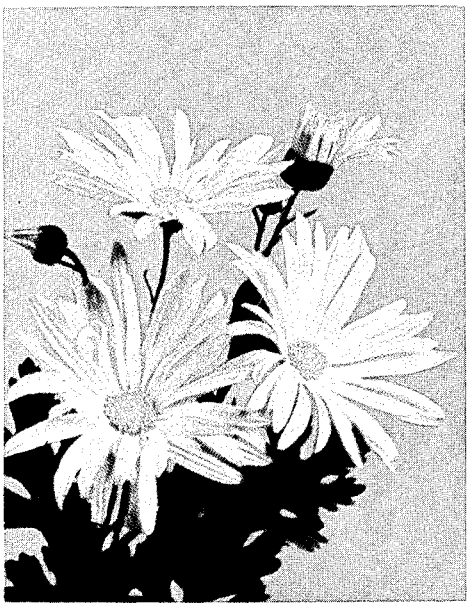
Figure 3:
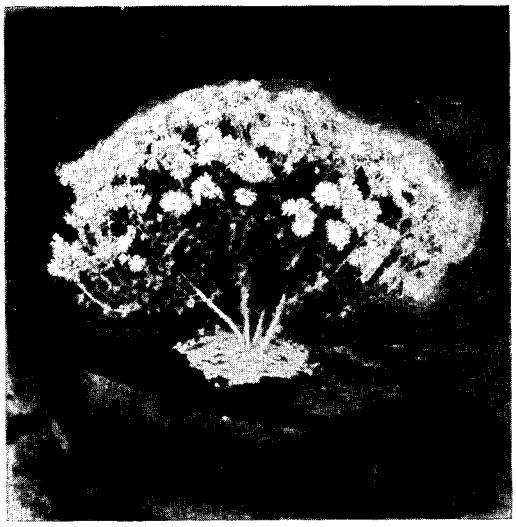
Figure 4:
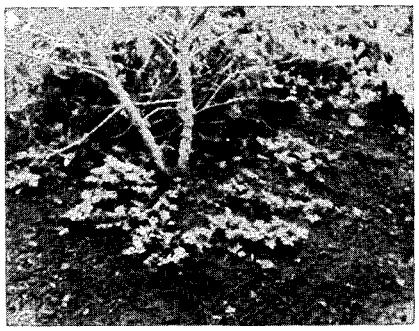

My invention relates to improvements in hardy perennial chrysanthemums and consists of a new and improved variety, differing radically in plant form and growth features from previously known chrysanthemums, with the single exception of the variety Astrid (and descendants) which is the parent of the present variety, from which it differs in important respects. This new variety has a blossom of more attractive color than its parent and has less tendency to fade or to produce non-blooming stems on young plants.

This new variety was obtained by the inventor from seed produced by self-fertilization of the variety Astrid, which is itself a hybrid of *Chrysanthemum articum* with an unknown variety of hardy garden chrysanthemum, and which originated on my property in Concordville. I planted the seeds of Astrid from which a large number of seedlings were produced. In the mass these seedlings exhibited certain variations in such numbers as to indicate them to be the second generation of a true hybrid. This new variety was selected from the seedlings and when asexually reproduced retained its distinguishing characteristics.

The fundamental improvement which distinguishes this new class of chrysanthemums is found in the plant and crown growth. The crown produces numerous underground stems which assure the winter-hardiness of the variety and which are capable of producing new plants which will, under conditions to be described, bloom normally in the spring. The plants of this new variety may be lifted in mid-winter and divided, and plants so made may be grown indoors and will produce normal flowers of dependable quantity and quality about the month of May, on stems approximately 16 inches in height. This feature is inherent in the race of hybrid chrysanthemums of which this variety is a member and especially serves to set this variety apart from chrysanthemums of previously known types, in which the feature was at best sporadic and abnormal.

The accompanying illustrations give a black-and-white portrayal of the plant indicating particularly the crown growth, together with a colored portrayal of the spring blossoms and the fall blossoms. Fig. I shows typical fall flowers; Fig. II, typical spring flowers; Fig. III, the plant as it appears in the fall; and Fig. IV, the crown growth as it appears in the fall.

In the following detailed description of this new variety of chrysanthemum, color plate references indicate Ridgway's Color Standards and Nomenclature. Where no plate numbers are given the ordinary dictionary terms are intended.

The plant of this variety is exceptionally vigorous and grows into perfect compact globe-shape without shearing or pinching. It is extremely hardly as a result of the vigorous and early crown growth, and is perfectly winter-hardy at Concordville, Pennsylvania.

The plant blooms more freely than most single chrysanthemums, and the many narrow petals of the blossoms give a lacy appearance contrasting with most other single chrysanthemums. There is a striking resemblance to the flowers of the Gerberas, which effect is heightened by the finely-cut leaves of the plant.

*The plant*

Growth: The plant of one year averages a height of 30 inches and width of 40 inches.

*Sprays.*—The stems are naturally well branched about 3 to 9 inches above ground. There are formed about 100 sprays, each containing 5 or 6 flowers, thus making a compact globe of blossoms.

*Crown.*—During a season the crown or rosette growth becomes 10 to 16 inches wide, the tips of underground stems emerging with small foliage ¼ to 2 inches above the surface.

*Foliage.*—Leaf blade—usually 1 inch wide by 1½ inches long, divided almost to midrib into five lobes, margin of each of which has sharp and multiple cuts ⅛ to ¼-inch deep. Petiole—one-half inch long. Color—upper side Elm Green (Plate XVII). Under side Light Hellebore Green (Plate XVII).

*Stems.*—Branching. Color—Light Hellebore Green (Plate XVII) with slight reddish tinge on sunny side. Size—medium. Strength—stiff and sturdy.

*Blooming.*—Season starts between October 1 and October 15 in my gardens.

*The flower*

Blossom:

*Size.*—Usually 2½ to 3½ inches across.

*Form.*—Irregularly double row of 35 to 60 ray flowers surrounding a raised center or cushion about ½ inch across.

*Ray flowers.*—Size 7/16 to 9/16 inch wide by 1 to 1½ inches long. Shape—uniform width until tapering, near tip, to a blunt point. Texture—quite thin, with parallel ridges which disappear with age. Color of fall flowers—Salmon Color to Apricot Buff (Plate XIV) with the buds and younger flowers ranging through Apricot Orange to Ferruginous (Plate XIV). The typical flower is between Salmon Color and Flesh Ocher (Plate XIV). Color of spring flowers—typical spring flowers are approximately Light Vinaceous Cinnamon (Plate XXIX).

*Cushion.*—The cushion or raised center is in standard concentric pattern of Compositae, and is composed of many pollen-bearing florets.

*Florets.*—Most of the florets have pistils with branched top which extends 1/8 inch beyond the corolla. Size—average 3/16 inch in length, exclusive of pistil. Color—Wax Yellow (Plate XVI).

Having thus disclosed my invention, I claim:

A new and distinct variety of perennial chrysanthemum substantially as shown and described, characterized particularly by its vigor and hardiness; its free-blooming habit; its well-balanced globe shape; its finely cut leaves; its unusual crown growth which enables it to normally produce flowers in the spring as well as in the fall; and its blossoms with narrow, lacy rayflowers, the color of which is Salmon to Ferruginous in the fall and lighter tints of the same colors in the spring.

JOHN FRANKLIN STYER.